United States Patent [19]

Seki

[11] Patent Number: 5,466,417

[45] Date of Patent: Nov. 14, 1995

[54] STERILIZER USING HIGH TEMPERATURE STEAM

[75] Inventor: Masahiro Seki, Tokyo, Japan

[73] Assignee: Tomi Seiko Co., Ltd., Tokyo, Japan

[21] Appl. No.: 151,378

[22] Filed: Nov. 12, 1993

[30] Foreign Application Priority Data

Nov. 13, 1992 [JP] Japan .................................. 4-303595

[51] Int. Cl.$^6$ .......................... G05D 23/32; G05B 15/00; A61L 2/06; B01B 1/00
[52] U.S. Cl. ............................ 422/109; 422/26; 422/298; 422/307
[58] Field of Search ............................ 422/26, 108–111, 422/307, 298

[56] References Cited

U.S. PATENT DOCUMENTS

| | | | |
|---|---|---|---|
| 4,164,538 | 8/1979 | Young et al. ............................. | 422/26 |
| 4,238,447 | 12/1980 | Wolff ...................................... | 422/26 |
| 4,261,950 | 4/1981 | Bainbridge et al. ...................... | 422/26 |
| 4,284,600 | 8/1981 | Gillis ........................................ | 422/26 |
| 4,471,790 | 9/1984 | Davis, Jr. et al. ...................... | 131/301 |
| 4,687,635 | 8/1987 | Kaehler et al. .......................... | 422/26 |
| 4,759,909 | 7/1988 | Joslyn ...................................... | 422/26 |
| 5,132,084 | 7/1992 | Harrel et al. ............................ | 422/26 |
| 5,145,642 | 9/1992 | Feathers, III et al. .................... | 422/26 |
| 5,164,161 | 11/1992 | Feathers et al. ........................ | 422/26 X |

*Primary Examiner*—Robert J. Warden
*Assistant Examiner*—E. Leigh Dawson
*Attorney, Agent, or Firm*—Jacobson, Price, Holman & Stern

[57] ABSTRACT

A sterilizer using steam, which can assure maintaining the temperature at the inside of a thing to be sterilized at a sterilizing temperature during a predetermined period, is proposed. The time to maintain the steam temperature at boiling, temperature is determined as a function of the time which was necessary to raise the steam temperature from a predetermined starting temperature to a predetermined end temperature. After maintaining the boiling temperature, a valve is closed to raise the steam temperature to the sterilizing temperature, which sterilizing temperature is maintained during a predetermined time period.

3 Claims, 4 Drawing Sheets

5,466,417

STERILIZER USING HIGH TEMPERATURE STEAM

FIELD OF THE INVENTION AND RELATED ART STATEMENT

The invention relates to a sterilizer using high temperature steam comprising: a pressure vessel for holding a thing to be sterilized in it, a high temperature steam generator having a heater for generating high temperature steam in the pressure vessel, a temperature sensor for measuring the temperature in the pressure vessel and a valve for controlling the communication between the inside and outside of the pressure vessel, whereby heating at a valve closed state, the temperature in the pressure vessel is maintained at a predetermined value during a predetermined time for perfect sterilization of the thing to be sterilized.

In Japanese provisional open laid utility model application SHO62-139535, a conventional sterilizer using high temperature steam is disclosed in which a thing to be sterilized is held in a pressure vessel, the vessel is gas-tightly closed, a high temperature is generated in the vessel by heating the inside using a heater at a valve opened state, the air is driven out from the inside of the vessel to the outside by filling the inside with steam. After that the valve is closed and the temperature in the pressure vessel is maintained at a predetermined value during a predetermined time, by heating the inside using the heater at a valve closed state.

FIG. 2 shows schematically the time variation of the temperature Ti in a thing to be sterilized and the temperature To of the steam in the pressure vessel.

The temperature sensor is installed, for example, on the inner surface of the pressure vessel to measure the steam temperature. At first the valve communicating the inside and the outside of the vessel is opened so as to let go out the air from the inside of the vessel to the outside, in other words, the inside of the pressure vessel is heated at the atmospheric pressure.

Accordingly the steam temperature in the vessel rises A to B along the solid line in FIG. 2. At the temperature $T_B$ which is the boiling temperature at atmospheric pressure, it reaches equilibrium to maintain a constant steam temperature $T_B$.

The valve is closed, so that the steam temperature rises again C to D along the solid line.

After reaching to the predetermined sterilizing temperature Ts at the point D, the temperature is maintained during a predetermined period Ts. At point E where this period is over, the power supply to the heater is cut off. As a result, the steam temperature in the vessel falls from E to F along the solid line.

By heat transfer, convection and radiation, the inner temperature Ti of the thing to be sterilized follows the steam temperature To with a time lag, as shown by a broken line in FIG. 2; the inner temperature Ti begins to rise not at point A but at point P, and reaches to the predetermined sterilizing temperature Ts not at point D but at point Q.

Passing a predetermined period Ts from the moment when the steam temperature reaches to Ts, the power supply of the heater is cut off. As a result, the steam temperature To and the temperature of the thing to be sterilized begin to fall at the point E. This means that the period, in which the inner temperature Ti of the thing to be sterilized is maintained at the predetermined sterilizing temperature Ts, is from the point Q to the point E, and this is shorter than the predetermined sterilizing period Ts.

Consequently, an insufficient sterilization may occur at the inside of the thing to be sterilized.

This can be avoided by making longer the predetermined period Ts for the predetermined sterilization temperature Ts.

The sterilization using steam is applied not only for reuse of contaminated equipment but also for the waste disposal of contaminated equipment. Thus the things to be sterilized are various. They may be solid things, for example, glass vessels, metal vessels, linen, or liquid, for example, culture medium in a vessel.

If the sterilization period Ts might be made longer in a general way, there may be the case that high temperature period is maintained longer in vain, or the case that the sterilization period Ts is insufficient.

It may be possible to solve such problems by inserting a temperature sensor into the objects or things which are to be sterilized. However, the mechanical structure of many things, which are to be sterilized, often prevents the insertion of a temperature sensor. Also, the expense of inserting a temperature sensor into the structure of many things, which are to be sterilized, is often prohibitive.

OBJECT AND SUMMARY OF THE INVENTION

The object of the present invention is to provide a sterilizer using a high temperature steam which maintains a predetermined sterilizing temperature at the inside of the various things to be sterilized during a predetermined period, and the period can be determined on the basis of the temperature of the steam in the vessel.

According to the present invention, the above mentioned problem is solved by a sterilizer using a high temperature steam comprising: a pressure vessel for holding a thing to be sterilized in it, a high temperature steam generator having a heater for generating high temperature steam in the pressure vessel, a temperature sensor for measuring the temperature in the pressure vessel and a valve for controlling the communication between the inside and outside of the pressure vessel, whereby heating at a valve closed state, the temperature in the pressure vessel is maintained at a predetermined value during a predetermined time for perfect sterilization of the thing to be sterilized, characterized in that it comprises: a RAM memory for storing the data of the time sequence of the temperature To of the steam in the vessel, a ROM memory for storing data of temperature rising retardation at the inside of a thing to be sterilized against the temperature rising of the steam in the vessel as a function of a period which is necessary to raise the steam temperature from a predetermined starting temperature to a predetermined end temperature, and a central control circuit which calculates the period for temperature rising of the steam in the vessel from said predetermined starting temperature to said predetermined end temperature, reads out the temperature rising retardation from said ROM on the basis of said calculated period for temperature rising, determines a period in which the steam temperature shall be maintained at the boiling temperature $T_B$ after reaching said boiling temperature, sends a signal to close said valve to a valve controller after passing said period to maintain the boiling temperature, and sends a signal to a heater controller to maintain the predetermined sterilizing temperature Ts during said predetermined period after reaching to this temperature.

As shown in FIG. 2, the difference ΔTs between the period Ts in which the temperature of the steam in the vessel is maintained at the sterilizing temperature Ts and the period in which the temperature at the inside of the thing to be sterilized is maintained at the sterilizing temperature Ts is substantially equal to the difference $t_B$ between the retardation $\Delta t$ of the temperature To at the inside of the thing to be sterilized against the temperature To of the steam in the vessel and the period $t_E$ in which the steam temperature is maintained at the boiling temperature $T_B$.

This relation can be expressed mathematically as follows:

$$\Delta t_B = \Delta t - t_E$$

$$\Delta \Delta t_S = \Delta t_B$$

This means that one gets $\Delta t_S = 0$, by making $\Delta t = t_E$. In other words, by maintaining the temperature of the steam to be the boiling temperature $T_B$ during a period substantially equal to the retardation $\Delta t$, the temperature at the inside of the thing to be sterilized can be maintained at the predetermined sterilizing temperature Ts during the predetermined period.

Thus, it is necessary to know the retardation $\Delta t$ of the temperature Ti at the inside of the thing to be sterilized against the temperature To of the steam.

This retardation depends upon the material, form and quality of the thing to be sterilized. It may be possible to measure previously the data of $\Delta t$ for various material, form and quality and to store them in a ROM, etc. However, it is not realistic.

According to the present invention, the retardation At is obtained, starting from an empirical fact that the retardation time $\Delta t$ is a function of the period which is necessary to raise the steam temperature from a predetermined starting temperature to a predetermined end temperature.

By the way, this empirical fact may be explicated theoretically as follows:

Suppose heat transfer coefficient be K, specific heat be C, density be p, temperature be θ, spacial co-ordinates be x, y, z, time be t, the heat transfer equation is expressed as follows.

$$\partial \theta / \partial t = \nabla (K \cdot \nabla \theta)/c\rho$$

where $$\nabla = (\partial/\partial x, \partial/\partial y, \partial/\partial z)$$

By first order approximation, the following equation stands $$\partial \theta / \partial t = \nabla ((K/c\rho) \cdot \nabla \theta)$$

The parameters determining the temperature change at a point in a space and the temperature difference at two points in a space are commonly the quantity (K/cρ). Thus there is a correlation function between the temperature rising velocity at a point in a space and the retardation of temperature rising at two points in a space.

According to the present invention, the relationship between the period which is necessary to raise the temperature of the steam in the vessel from a predetermined starting temperature to a predetermined end temperature and the retardation time of temperature rising at the inside of a thing to be sterilized is previously measured and is stored in a ROM memory.

When this apparatus is used, the time sequence of the steam temperature is stored in a RAM memory, and the temperature rising velocity is calculated based on the data in this RAM memory.

The retardation of temperature rising is read out from the ROM memory according to this temperature rising velocity.

The period $t_B$ to maintain the temperature at the boiling temperature $t_B$ is determined as a function of this retardation. It is determined, for example, as a sum of this retardation plus a constant value.

The steam temperature is maintained at the boiling temperature during this period $t_B$ after reaching this temperature. As a result, the temperatures of steam and the inside of the thing to be sterilized become substantially equal.

After closing the valve, the vessel is further heated. The times required to reach to the sterilizing temperature is substantially equal for the steam and the inside of the things. Because both of them start from the same boiling temperature.

Consequently, if the steam temperature is maintained at the sterilizing temperature Ts during a predetermined time $t_S$, also the temperature of the inside of the thing to be sterilized is maintained at the sterilizing temperature during the same period.

Of course, the inside of the thing to be sterilized and the steam is situated at separated points in a space, thus their temperature cannot be exactly the same, however, it can be substantially the same. Or by designing with a margin of safety, one can obtain the sterilization effect as expected.

DETAILED DESCRIPTION OF PREFERRED EMBODIMENTS

Figure 1:
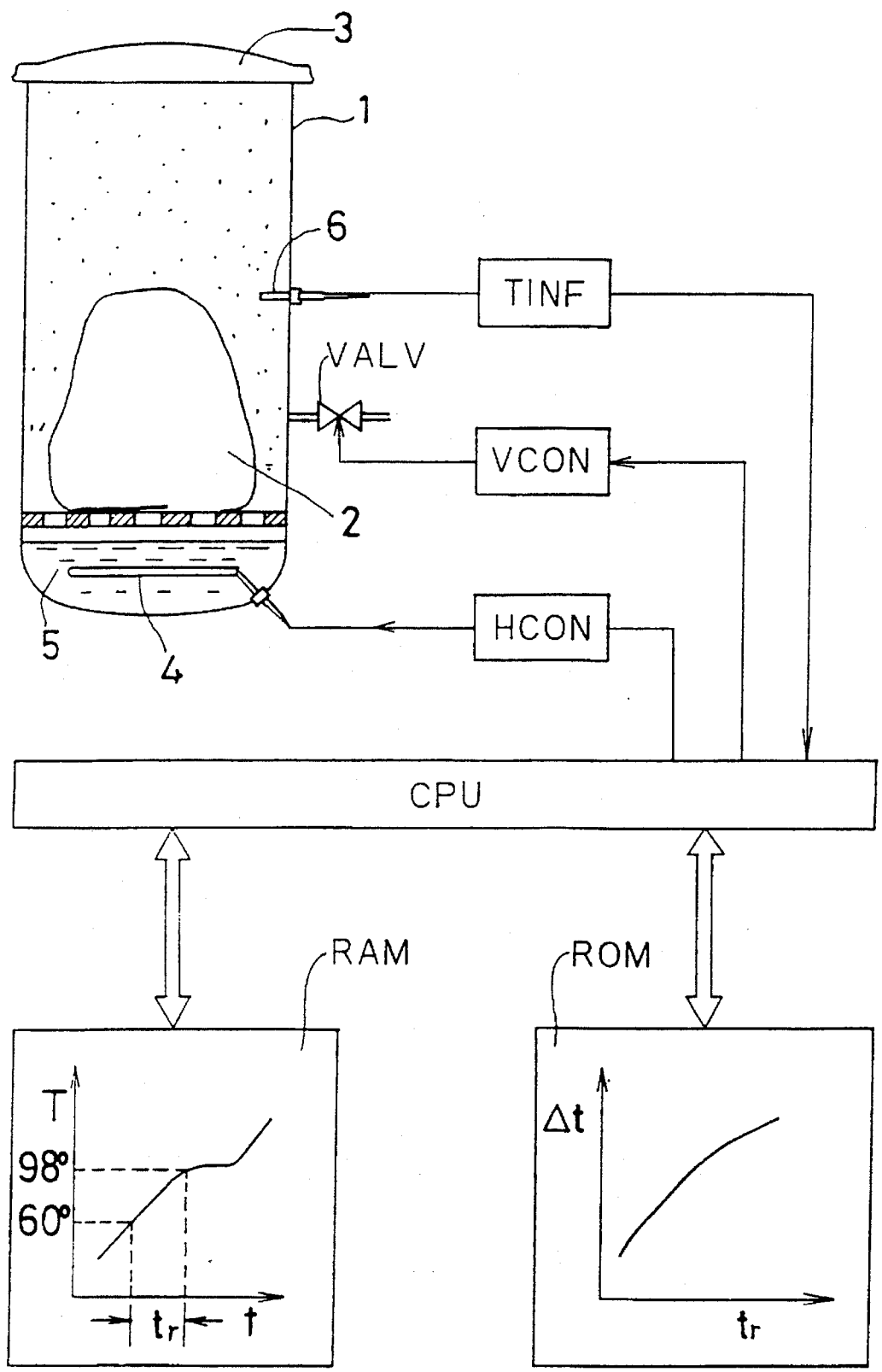
FIG. 1 is a block diagram of a sterilizer using a high temperature steam according to the present invention.
Figure 2:
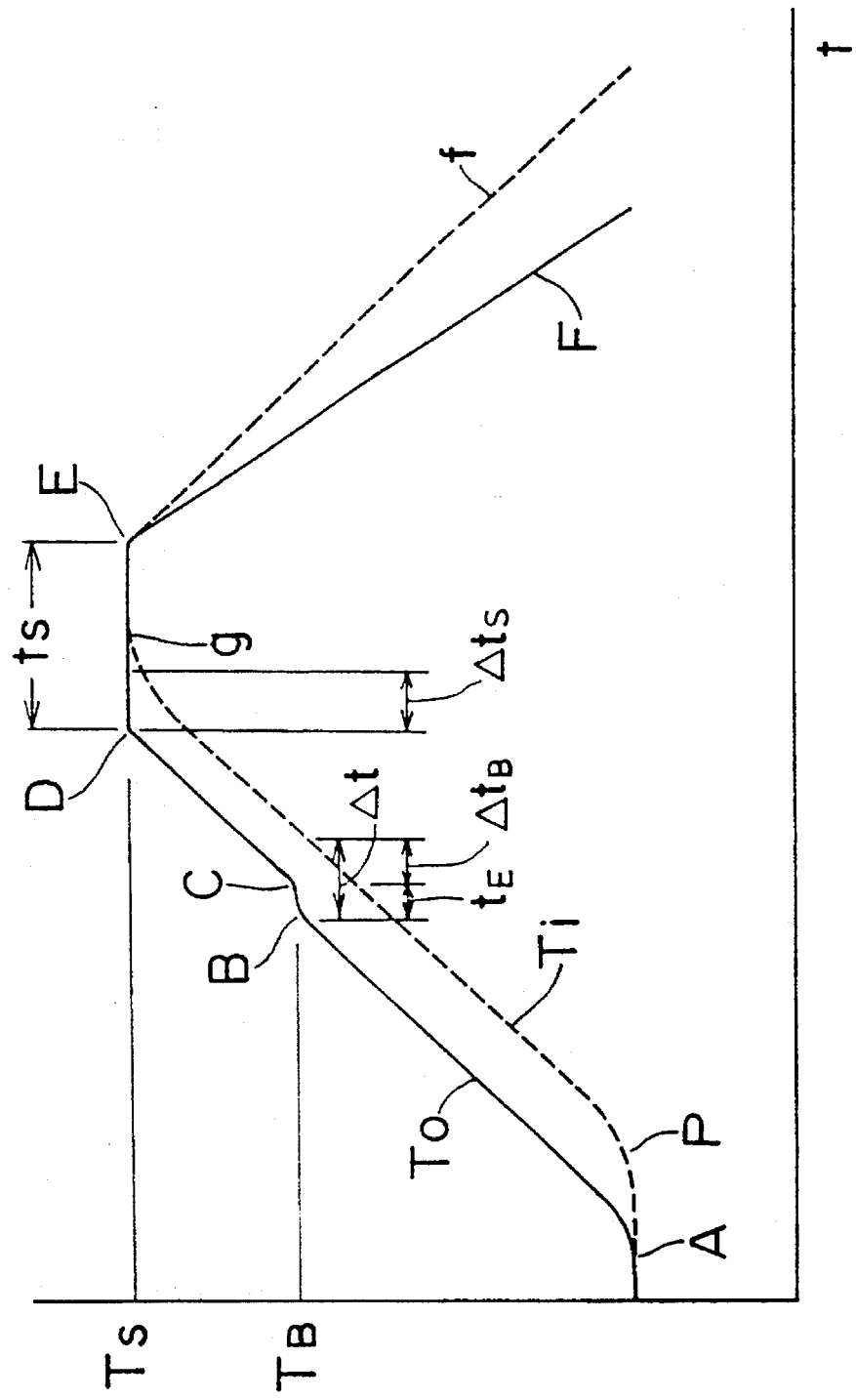
FIG. 2 is a graph showing the relation between the temperature of steam in the vessel and the temperature at the inside of a thing to be sterilized in a conventional sterilizer using high temperature steam.

FIG. 1 is a block diagram of a sterilizer according to the present invention.

A thing 2 to be sterilized is held in a pressure vessel 1, the latter is sealed with a cover 3.

There is a steam generator 5 having a heater 4 at the under part of the pressure vessel 1. The heater 4 is controlled by a heater controller HCON. A valve VALV communicating the inside and the outside of the vessel 1 is installed at the side wall of the pressure vessel 1. The valve is controlled by a valve controller VCON. A temperature sensor 6 is arranged at the inside of the pressure vessel 1.

At first, the valve VALV is opened using the valve controller VCON, and the pressure vessel is heated using the heater 4. The temperature at the inside of the vessel 1 is raised by steam generated by the steam generator 5.

The steam temperature is measured by the temperature sensor 6, and its output is sent to a central control circuit CPU through a temperature data interface TINF, and as a function of a time t they are stored in a RAM memory.

A time interval tr defined as the time which was necessary to raise the temperature from a predetermined starting temperature (for example, 60° C.) to a predetermined end temperature (for example, 98° C.) is calculated at the central control unit CPU using the data stored in the RAM memory.

In a ROM memory, retardation time $\Delta t$ of temperature rising at the inside of the thing to be sterilized against the steam temperature Ti are stored as a function of a time tr.

The retardation time Δt corresponding to the calculated time tr is read out from the ROM memory ROM.

The time te to maintain the temperature at the boiling temperature $t_B$ is determined according to this retardation time Δt. It may be possible to store directly in the ROM memory the time to maintain the temperature at the boiling temperature in place of the retardation time Δt.

Figure 3:
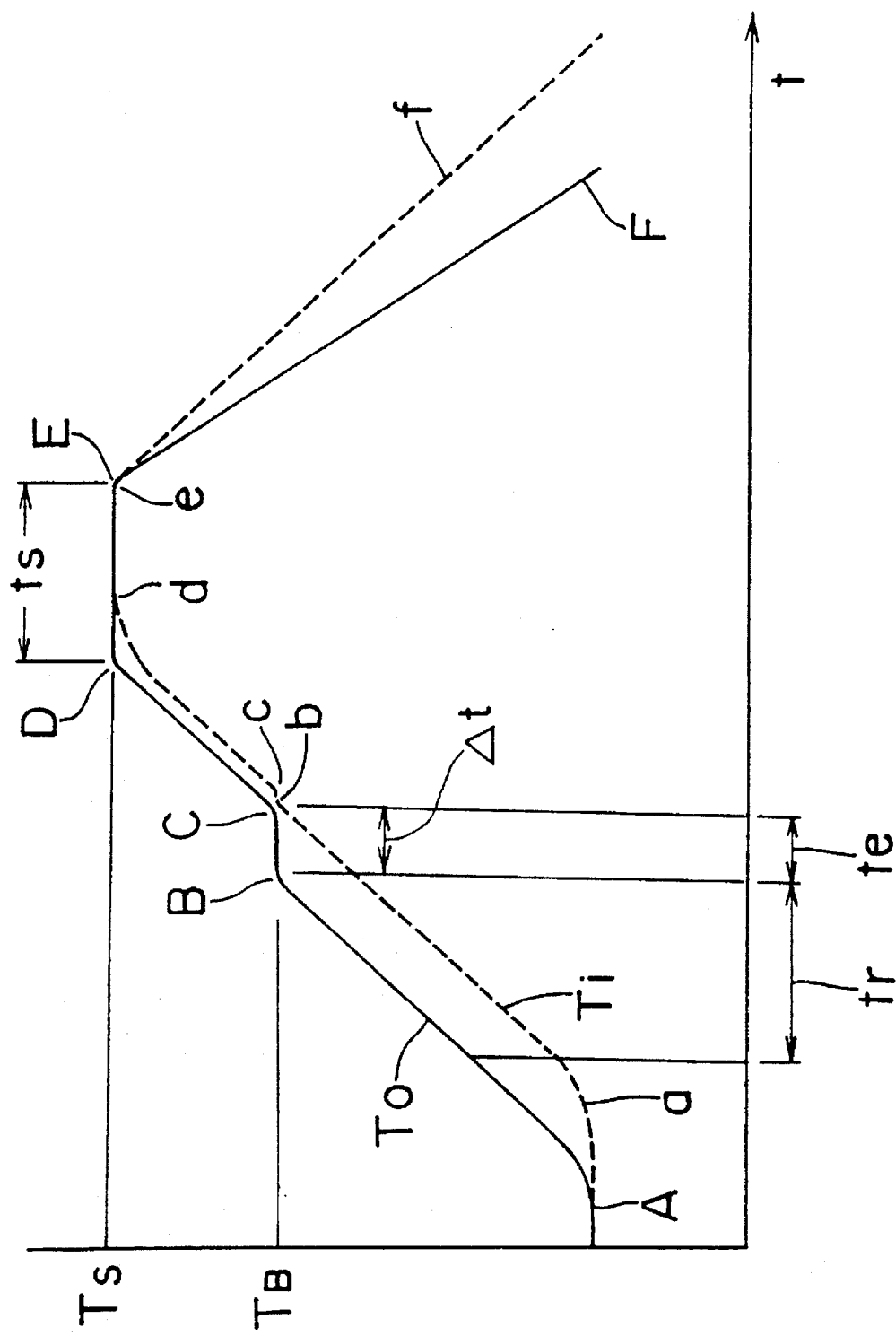
FIG. 3 is a graph showing the relation between the temperature of steam in the vessel and the temperature at the inside of a thing to be sterilized in a sterilizer according to the present invention.

The steam temperature is maintained at the boiling temperature $T_B$ during the period te. Namely the steam temperature To rises along the solid line in FIG. 3, from the point A to the point B, and the boiling temperature is maintained during the time interval te. On the other hand, the temperature Ti at the inside of the thing to be sterilized begins to rise at the point a and reaches to the boiling temperature $t_B$ at the point b where the temperature is equal to the steam temperature.

The valve is closed at this moment, however the heating is continued. Thus the temperature To in the vessel increases along the solid line from the point C to the point D, and reaches to the sterilizing temperature Ts (for example 120° C.) at the point D.

Also the temperature Ti at the inside of the thing to be sterilized rises along the broken line from point b to the point d with a little retardation time, and reaches to the sterilizing temperature Ts at the point d.

Different from a conventional sterilizer, the steam temperature at the point C and the temperature at the inside of the thing to be sterilized is equal, the retardation between the moment when the steam temperature To becomes the sterilizing temperature Ts and the moment when the temperature Ti at the inside of the thing to be sterilized becomes the sterilizing temperature Ts is small.

After maintaining the steam temperature To to be equal to the sterilization temperature Ts during a predetermined period (for example, 20 minutes), the power supply to the heater is cut off at the point E.

The temperature Ti at the inside of the thing to be sterilized and the steam temperature To fall down respectively along the broken line and the solid line, to the point f and to the point F.

Figure 4:
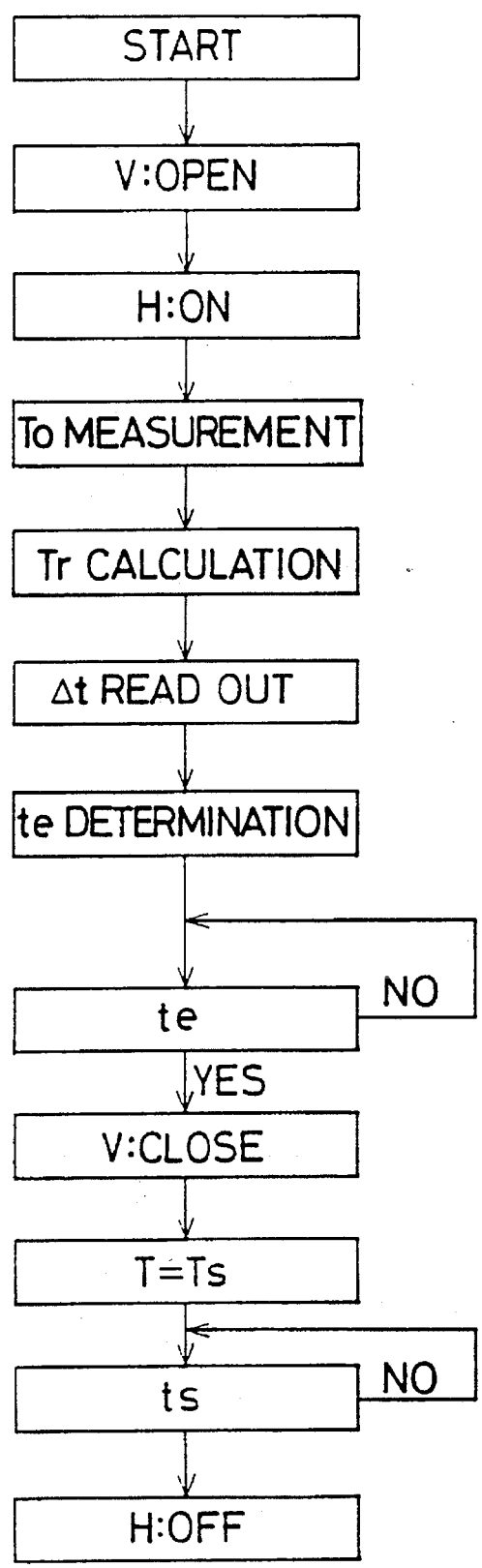
FIG. 4 is a flow chart showing the procedure of function of the sterilizer according to the present invention.

FIG. 4 is a flow chart of the procedure of function of a sterilizer according to the present invention.

The procedure can be summed up as follows.:
1) START the procedure begins
2) V:OPEN the valve is opened
3) H:ON the power supply to the heater begins
4) To:measurement the steam temperature is measured and the data are stored in a RAM memory
5) tr:calculation the time tr, which was necessary for that the steam temperature To rises from a predetermined starting temperature to a predetermined end temperature, is calculated based on the data in the RAM memory.
6) Δt read out the retardation time Δt corresponding to the calculated time tr is read out from a ROM memory.
7) determination of te the time te for maintaining the steam temperature at the boiling temperature is determined according to the read out retardation time ΔT
8) period te the steam temperature is maintained at the boiling temperature during the period te.
9) V:CLOSE the valve is closed
10) T=Ts reaching to the sterilizing temperature
11) period ts temperature maintenance at the sterilizing temperature during a predetermined period ts
12) H:OFF the power supply to the heater is cut off An electromagnetic valve, or a valve having a bellows to be actuated by vaporization of alcohol and so on, may be available, as a valve in a sterilizer according to the present invention.

The sterilizer according to the present invention can comprise not only the ROM and RAM memories mentioned above, but also conventional ROM or RAM memories necessary for the functions of the central control unit CPU.

The velocity of the temperature rising of the steam can be measured without RAM memory: it can be replaced by a conventional time calculating counter which begins to count at a moment when the steam temperature becomes a predetermined temperature and ends counting at a moment when the steam temperature becomes a predetermined end temperature.

Using the sterilizer according to the present invention, the temperature at the inside of a various type of things to be sterilized can be maintained at the sterilizing temperature during a predetermined period. Accordingly a waste of time for a meaningless longer time sterilization or an insufficient shorter time sterilization can be avoided.

I claim:

1. A sterilizer using steam comprising
a pressure vessel for holding a thing to be sterilized,
a steam generator having a heater for generating steam in the pressure vessel,
a temperature sensor for measuring the temperature in the pressure vessel, and
a valve for controlling the communication between the inside and outside of the pressure vessel, whereby, when heating with the valve closed, the temperature in the pressure vessel is maintained at a predetermined value during a predetermined sterilization time for perfect sterilization of the thing to be sterilized, said sterilizer including:
a RAM for storing data of a time sequence of the temperature of the steam in the vessel,
a ROM with data, stored as a function of time, of the retardation time of rising temperature at the inside of the thing to be sterilized compared with the rising temperature of the steam, and
a Central Control Circuit which:
calculates the period for the rising temperature of the steam in the vessel from a predetermined starting temperature to a predetermined end temperature, from data stored in the RAM,
reads out the retardation time of rising temperature from said ROM on the basis of said calculated period for the rising temperature,
determines a period of time, according to the retardation time of rising temperature, in which the steam temperature is to be maintained at the boiling temperature after reaching said boiling temperature,
sends a signal to close said valve to a valve controller after maintaining the boiling temperature for said determined period of time, and
sends a signal to a heater controller to continue heating said vessel up to the predetermined sterilizing temperature and to maintain the predetermined sterilizing temperature during said predetermined sterilizing period after reaching the sterilizing temperature.

2. A sterilizer using steam comprising
a pressure vessel for holding a thing to be sterilized,
a steam generator having a heater for generating steam in the pressure vessel,
a temperature sensor for measuring the temperature in the pressure vessel, and
a valve for controlling the communication between the inside and outside of the pressure vessel, whereby, when heating with the valve closed, the temperature in the pressure vessel is maintained at a predetermined value during a predetermined sterilization time for perfect sterilization of the thing to be sterilized, said sterilizer includes a RAM for storing data of a time sequence of the temperature of the steam in the vessel, a ROM with data, stored as a function of time, of the retardation time of rising temperature at the inside of the thing to be sterilized compared with the rising temperature of the steam, and a Central Control Circuit which:
(i) calculates the period for rising temperature of the steam in the vessel from a predetermined starting temperature to a predetermined end temperature, from data stored in the RAM,
(ii) reads out the retardation time of rising temperature from said ROM on the basis of said calculated period for rising temperature, and wherein one of two conditions exist:

a first condition being
(i) said ROM stores data, corresponding to the retardation time of rising temperature, of a determined time period necessary to maintain the steam temperature at the boiling temperature after the steam temperature reaches the boiling temperature, and a second condition being
(ii) said central control circuit determines a time period, according to the retardation time of rising temperature, in which the steam temperature is to be maintained at the boiling temperature after reaching said boiling temperature, the Central Control Circuit, according to said one of two conditions
(iii) sends a signal to close said valve to a valve controller after maintaining the boiling temperature for said determined time period, and
(iv) sends a signal to a heater controller to maintain the predetermined sterilizing temperature during said predetermined sterilizing period after reaching the sterilizing temperature.

3. A sterilizer using steam comprising a pressure vessel for holding a thing to be sterilized, a steam generator having a heater for generating steam in the pressure vessel, a temperature sensor for measuring the temperature in the pressure vessel, and a valve for controlling the communication between the inside and outside of the pressure vessel, whereby, when heating with the valve closed, the temperature in the pressure vessel is maintained at a predetermined value during a predetermined sterilization time for perfect sterilization of the thing to be sterilized, said sterilizer including:

a counter for obtaining a period from the moment when the stem temperature reaches a predetermined starting temperature to the moment when the steam temperature obtains a predetermined end temperature, a ROM with data, stored as a function of time, of the retardation time of rising temperature at the inside of the thing to be sterilized compared with the rising temperature of the steam, and a Central Control Circuit which:
reads out the rising temperature retardation from said ROM on the basis of said time obtained in said counter,
determines a period of time in which the steam temperature is to be maintained at the boiling temperature after reaching said boiling temperature,
sends a signal to close said valve to a valve controller after maintaining the boiling temperature for said determined period of time, and
sends a signal to a heater controller to continue heating said vessel up to the predetermined sterilizing temperature and to maintain the predetermined sterilizing temperature during said predetermined sterilizing period after reaching the sterilizing temperature.

* * * * *